(12) United States Patent
Borghi

(10) Patent No.: US 8,932,304 B2
(45) Date of Patent: Jan. 13, 2015

(54) VASCULAR GRAFT

(75) Inventor: Enzo Borghi, Budrio (IT)

(73) Assignee: Newman Medical KFT, Budapest (HU)

( * ) Notice: Subject to any disclaimer, the term of this patent is extended or adjusted under 35 U.S.C. 154(b) by 100 days.

(21) Appl. No.: 13/168,433

(22) Filed: Jun. 24, 2011

(65) Prior Publication Data

US 2011/0264123 A1  Oct. 27, 2011

Related U.S. Application Data

(62) Division of application No. 11/012,568, filed on Dec. 15, 2004, now Pat. No. 8,038,690.

(30) Foreign Application Priority Data

Oct. 19, 2004 (IT) .............................. BO2004A0642

(51) Int. Cl.
  *A61B 17/10* (2006.01)
  *A61B 17/11* (2006.01)
  *A61B 17/115* (2006.01)

(52) U.S. Cl.
  CPC ............ *A61B 17/11* (2013.01); *A61B 17/1155* (2013.01); *A61B 2017/1107* (2013.01); *A61B 2017/1125* (2013.01)
  USPC ....................................................... 606/139

(58) Field of Classification Search
  CPC ................... A61B 17/1155; A61B 2017/1107; A61B 2017/1132; A61B 2017/1157
  USPC ................. 606/139, 142, 144, 148–151, 153; 227/175.1, 181.1; 600/36
  See application file for complete search history.

(56) References Cited

U.S. PATENT DOCUMENTS

| | | | |
|---|---|---|---|
| 3,254,650 A | 6/1966 | Collito | |
| 3,258,012 A * | 6/1966 | Nakayama et al. | ........... 606/150 |
| 3,316,914 A | 5/1967 | Collito | |
| 4,206,863 A | 6/1980 | Savino | |
| 4,214,586 A | 7/1980 | Mericle | |
| 4,476,863 A * | 10/1984 | Kanshin et al. | ................ 606/153 |
| 4,505,414 A * | 3/1985 | Filipi | ............... 227/19 |
| 4,603,693 A * | 8/1986 | Conta et al. | ................. 227/179.1 |
| 4,610,250 A | 9/1986 | Green | |
| 4,930,502 A | 6/1990 | Chen | |
| 4,997,439 A | 3/1991 | Chen | |
| 5,123,908 A | 6/1992 | Chen | |

(Continued)

FOREIGN PATENT DOCUMENTS

| | | |
|---|---|---|
| WO | 9008509 A1 | 8/1990 |
| WO | 0172232 A1 | 10/2001 |

OTHER PUBLICATIONS

Tozzi, P., et al., "Preliminary Clinical Experience With the Heartflo Anastomosis Device", Thorac. Cardiov. Surg., 2001, vol. 49, p. 279-282.

(Continued)

*Primary Examiner* — Katherine Dowe
*Assistant Examiner* — Jonathan Hollm
(74) *Attorney, Agent, or Firm* — Pearne & Gordon LLP

(57) ABSTRACT

A vascular graft for anastomosis of blood vessels or ducts comprises piercing means (3) for engaging an end portion (8/8') of a blood vessel or prosthesis and means (6, 6') for precisely guiding one or more piercing elements (3) to pierce the wall of the vessel or prosthesis to a predetermined depth and in a predetermined direction.

7 Claims, 13 Drawing Sheets

(56) References Cited

U.S. PATENT DOCUMENTS

| | | |
|---|---|---|
| 5,250,058 A | 10/1993 | Miller et al. |
| 5,346,501 A | 9/1994 | Regula et al. |
| 5,697,943 A | 12/1997 | Sauer et al. |
| 5,720,755 A | 2/1998 | Dakov |
| 6,030,392 A | 2/2000 | Dakov |
| 6,036,705 A | 3/2000 | Nash et al. |
| 6,110,187 A | 8/2000 | Donlon |
| 6,241,742 B1 * | 6/2001 | Spence et al. ............ 606/153 |
| 6,623,494 B1 | 9/2003 | Blatter |
| 6,736,824 B2 | 5/2004 | Borghi |
| 2001/0039425 A1 * | 11/2001 | Dakov ............ 606/153 |
| 2003/0088255 A1 | 5/2003 | Borghi |
| 2004/0102797 A1 * | 5/2004 | Golden et al. ............ 606/153 |
| 2005/0021053 A1 * | 1/2005 | Heinrich ............ 606/139 |
| 2005/0096676 A1 * | 5/2005 | Gifford et al. ............ 606/153 |

OTHER PUBLICATIONS

Tozzi, P., et al., "Sutureless Coronary Anastomoses: Revival of Old Concepts", European Journal of Cardio-Thoracic Surgery, 2002, vol. 22, p. 565-570.

Tozzi, P., et al., "Is the Graftconnector a Valid Alternative to Running Suture in End-To-Side Coronary Arteries Anastomoses?", Ann. Thorac. Surg., 2001, vol. 72, p. S999-1003.

International Search Report for International Application No. PCT/IB2004/004101 dated Jul. 26, 2005, pp. 1-4.

* cited by examiner

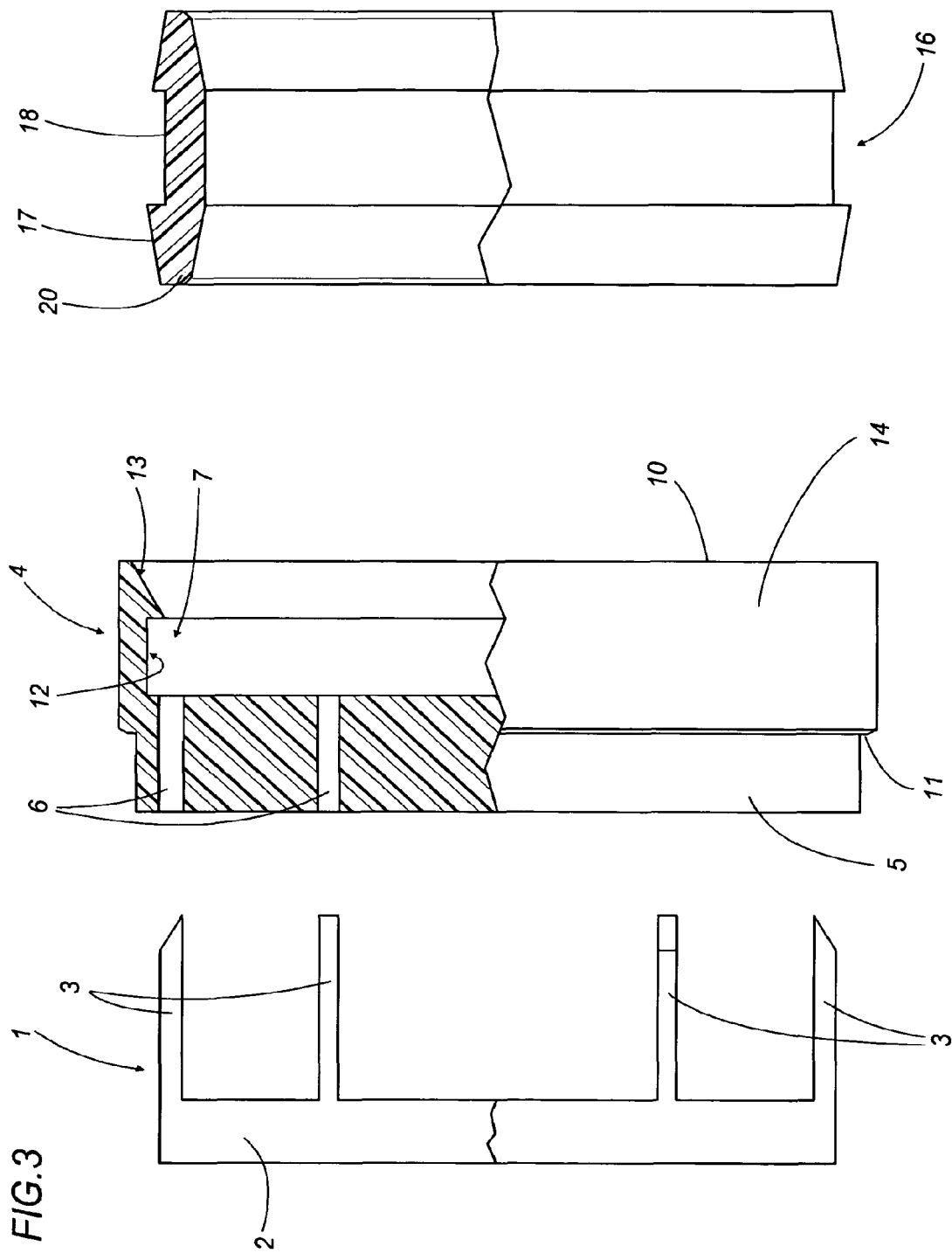

FIG.4a
FIG.4b
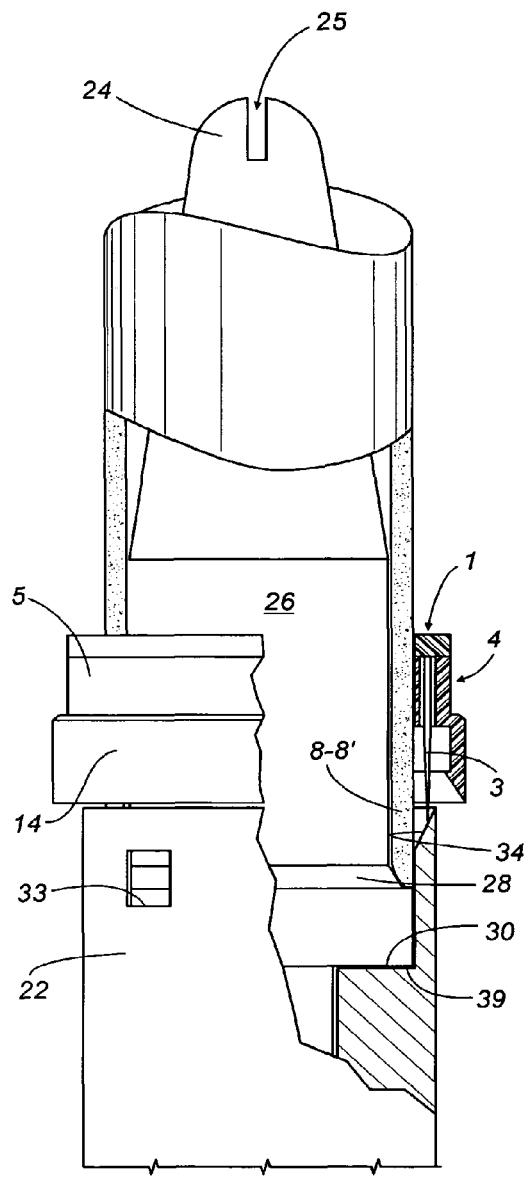
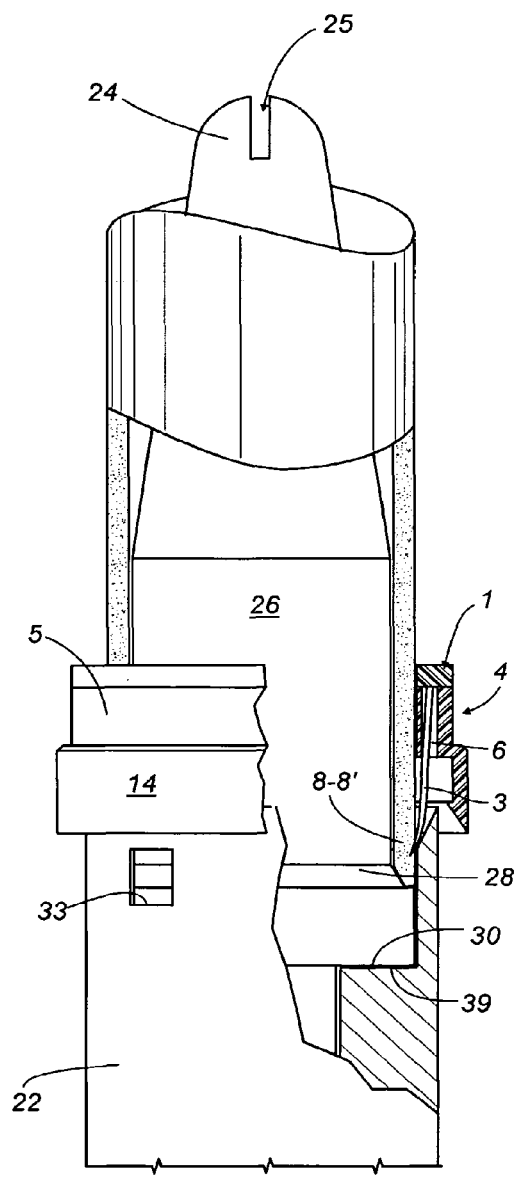

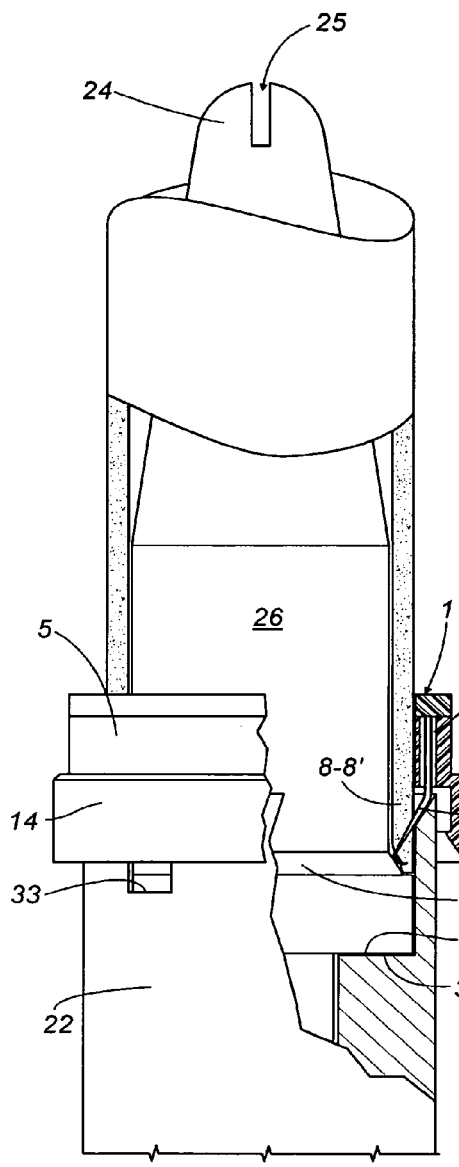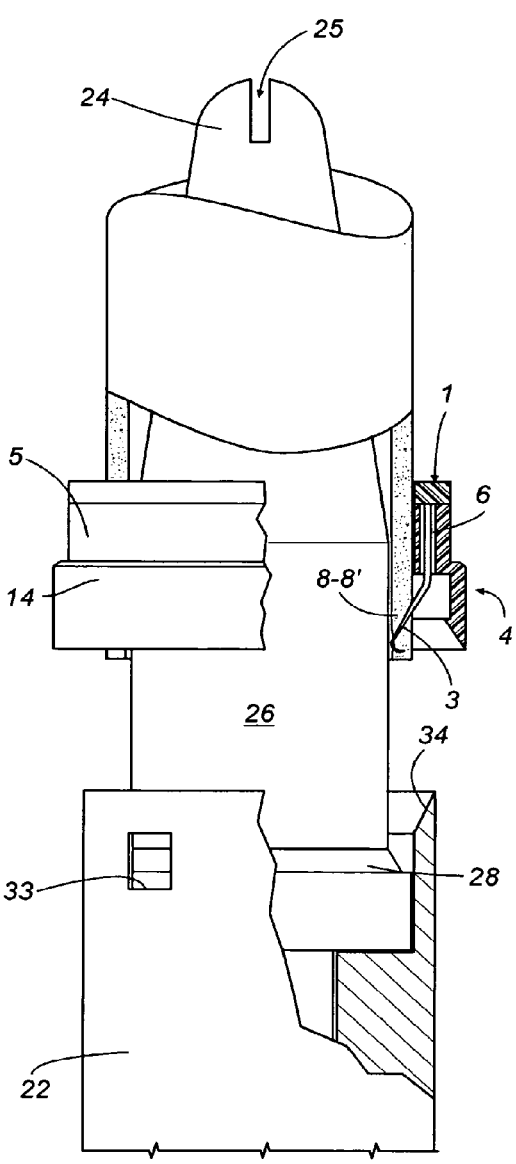

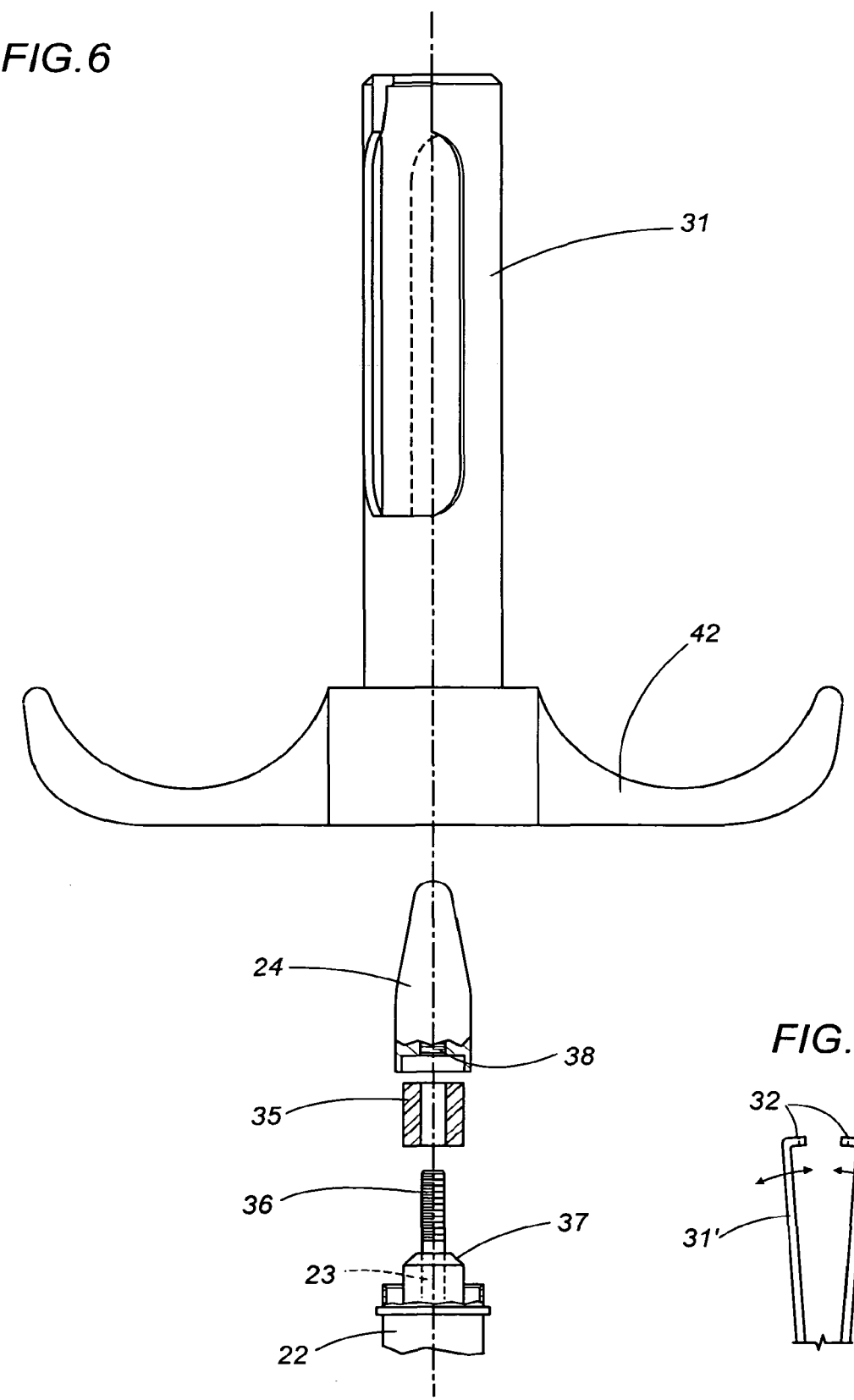

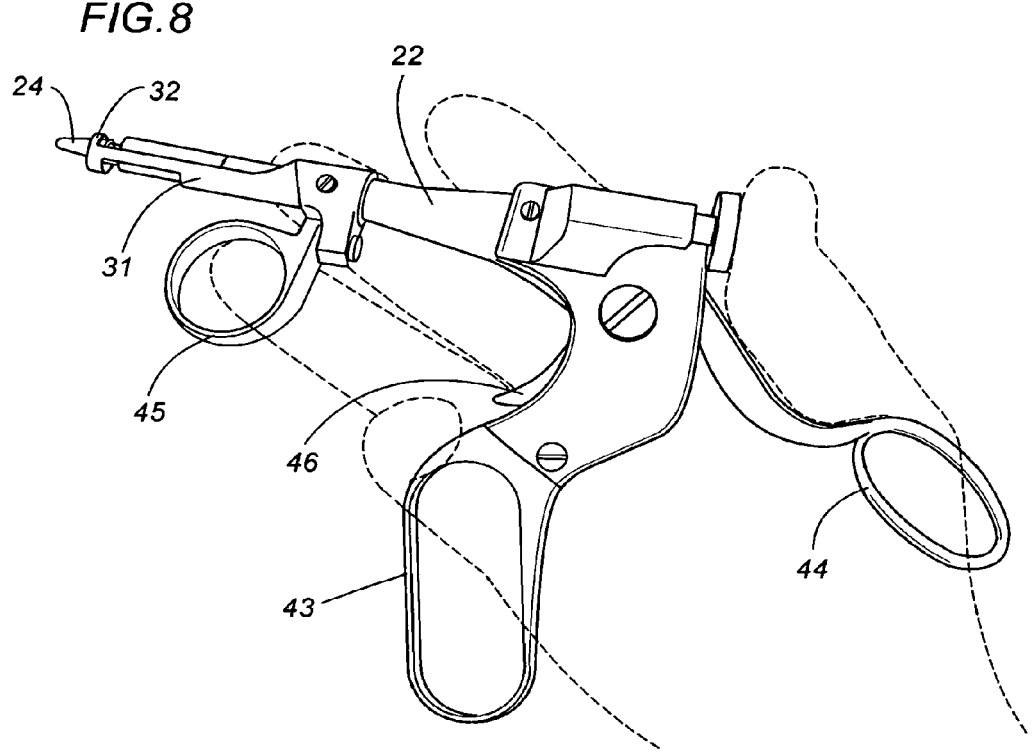
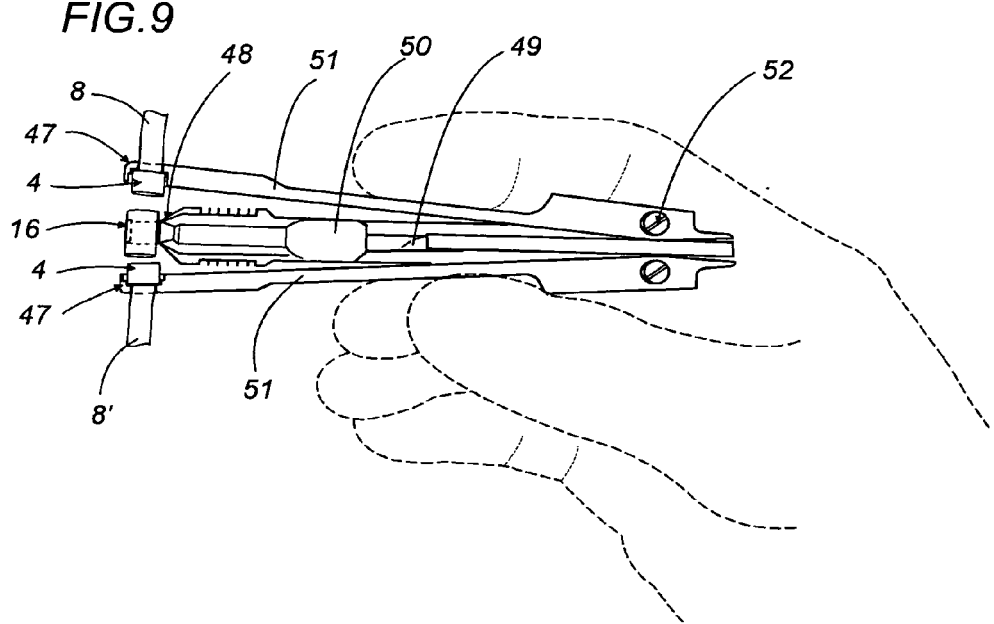

VASCULAR GRAFT

BACKGROUND OF THE INVENTION

The present invention relates to a vascular graft for anastomosis operations in which two hollow structures consisting of blood vessels or vascular prostheses are surgically connected.

In (particular, when the structures connected are the two ends of a blood vessel, a lymphatic vessel or other type of duct, the operation is called end-to-end anastomosis and its purpose is to restore flow to the vessel or duct.

This specification expressly refers to vascular anastomosis applied to the human body, without thereby restricting the scope of the invention.

The prior patent application B02000A000169 describes an apparatus for end-to-end anastomosis, designed by the same inventor as the graft of this invention, in which the means for mutually connecting the vessel portions to be anastomosed comprise circular staples that hold the ends of the vessel in place so that the edges of the vessel match perfectly.

This solution solves many of the problems that existed before its disclosure because, once implanted, it enables the vessel to be reconstructed completely.

Although application of the graft is simpler using this solution, the problem of the simplicity of application remains unsolved (and simplicity is of vital importance in vascular surgery).

Another problem is the accuracy with which the circular staple is applied. Once applied, the circular staples must neither lacerate the vessel nor obstruct blood flow which leads to clotting.

The present has for its primary aim to provide a vascular graft that overcomes the drawbacks of prior art due in particular to the relative complexity of use and accuracy of application to vessels or vascular prostheses.

Another aim of the invention is to provide a vascular graft that does not in any way obstruct blood flow in the anastomosed vessel.

SUMMARY OF THE INVENTION

These aims are achieved by a graft and an apparatus according to the main claim.

A first advantage of the invention is that contact between the connecting parts and the blood vessel is limited to the vessel wall, leaving the inside surface free and thus having no effect on the blood flow within the vessel.

Another advantage is the ability of the device to hold the edges of the vessel together securely and accurately.

Yet another advantage is due to the simplicity and rapidity of application to each edge of the vessel, thus significantly reducing the time required for the operation.

BRIEF DESCRIPTION OF THE DRAWINGS

The invention will now be described with reference to the accompanying drawings which illustrate a preferred embodiment of it and in which:

FIG. 3 is an exploded view of a second embodiment of the device according to the present invention;

FIGS. 4a-4d show successive steps in the use of the applicator of FIG. 4;

FIG. 6 is an exploded view of the applicator of FIGS. 5a and 5b;

FIG. 6a is a constructional detail view of an applicator;

FIG. 8 shows an embodiment of an applicator according to the invention, fitted with a handgrip;

FIG. 9 shows a pair of forceps for connecting the grafts applied to respective end portions of an anastomosed vessel;

DESCRIPTION OF THE PREFERRED EMBODIMENTS

Figure 1:
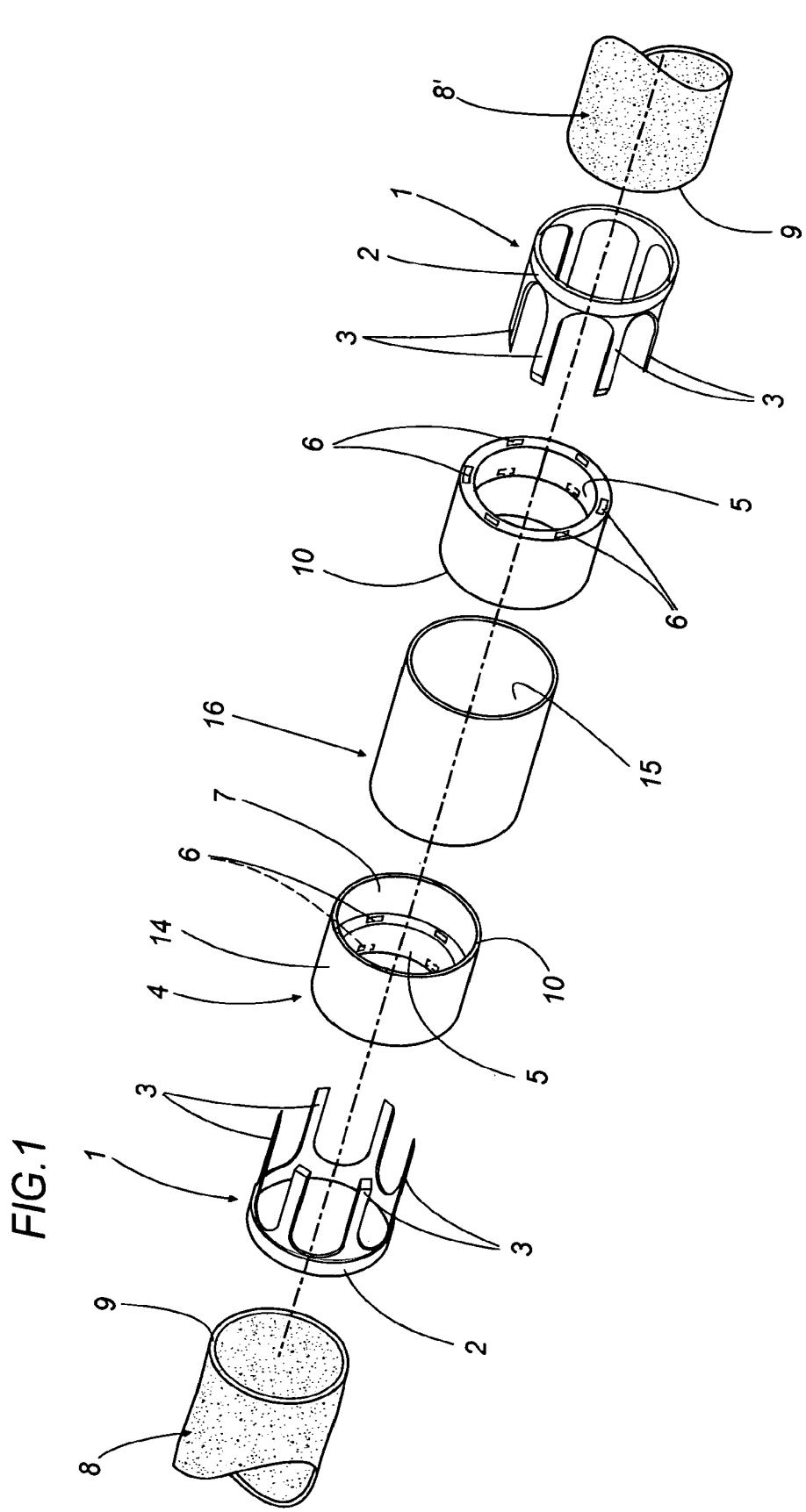
FIG. 1 is an exploded view of a first embodiment of a vascular graft according to the present invention applied to two end portions of a vessel to be anastomosed.
Figure 2:
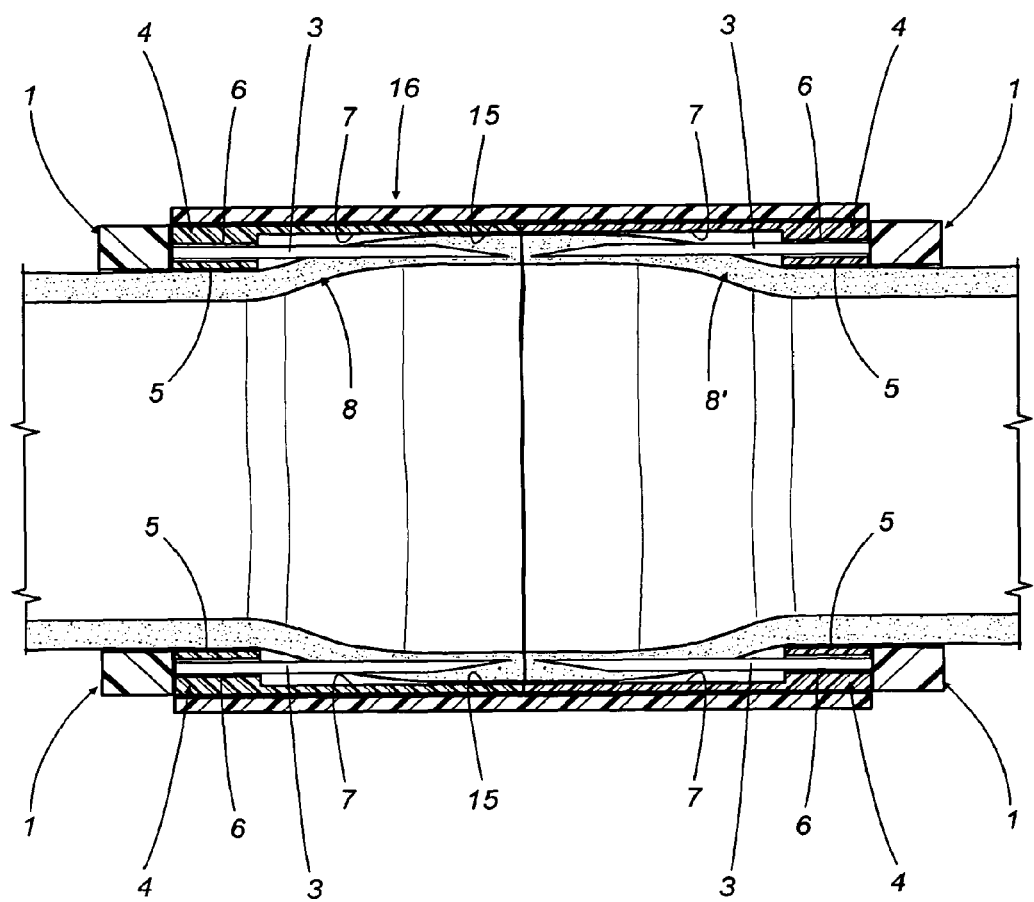
FIG. 2 is a cross section of the graft of FIG. 1 in a working configuration.

In the embodiment shown in FIGS. 1 and 2, the graft according to the invention comprises:

a first cylindrical element 1, or staple, consisting of a ring 2 and a plurality of longitudinal legs 3 protruding from the front of the ring 2;

a second cylindrical element 4 having a first portion 5 with a plurality of longitudinal holes 6 inside it, into which the legs 3 of the staple 1 can be inserted, if necessary with slight mechanical interference. The holes 6 are substantially parallel and end at a second portion 14 of the cylinder 4, at a predetermined distance from its inside surface 7.

In this solution, the walls 7 are advantageously used as a reference surface for positioning the outside surface of the end portion 8/8' of the vessel to be anastomosed so that when the vessel is pierced, the legs 3 are guided by the holes 6 and penetrate the vessel wall to a measured depth.

Further, the length of the legs 3 may be precisely predetermined in such a way that, once inserted, they are slightly inside the front edge 10.

In the embodiment of FIG. 1, the connecting elements 4 have a cylindrical outer surface 14 that permits interference fitting to the inside surface 15 of another cylinder 16 designed to bring together two staples 1 applied to respective end portions 8/8' of a vessel to be anastomosed.

Similarly, the size of the cylinders 4 and 16 can be varied to obtain an interference fit where the coupling cylinder 16 is inserted into the connecting cylinders 4.

The connecting cylinders 4 and/or the reciprocal coupling cylinder 16 can be made of Delrin® biocompatible plastic.

FIG. 3 shows a second embodiment of the invention, where the connecting cylinder 4 has an annular protrusion 11 and an inside surface 7 with an internal annular recess 12 and a tapered guide profile 13 extending to the front edge 10 of the connecting cylinder 4.

In this case, the reciprocal coupling cylinder 16 has end edges with guide profiles 17 shaped to match the corresponding profiles 13 and an external annular recess 18 that snaps into the internal recess 12 of the cylinders 4 to be joined together.

Advantageously, the coupling cylinder 16 has chamfered inside edges 20 designed to prevent interference with the legs 3 when the device is reciprocally coupled.

In this embodiment, too, the combination of recesses and protrusions may be different by varying the relative dimensions of the connecting cylinders 4 and reciprocal coupling cylinder 16, and different fastening means, comprising spring tabs for example, might also be used in addition to or instead of the plain interference fit.

Figure 3A:
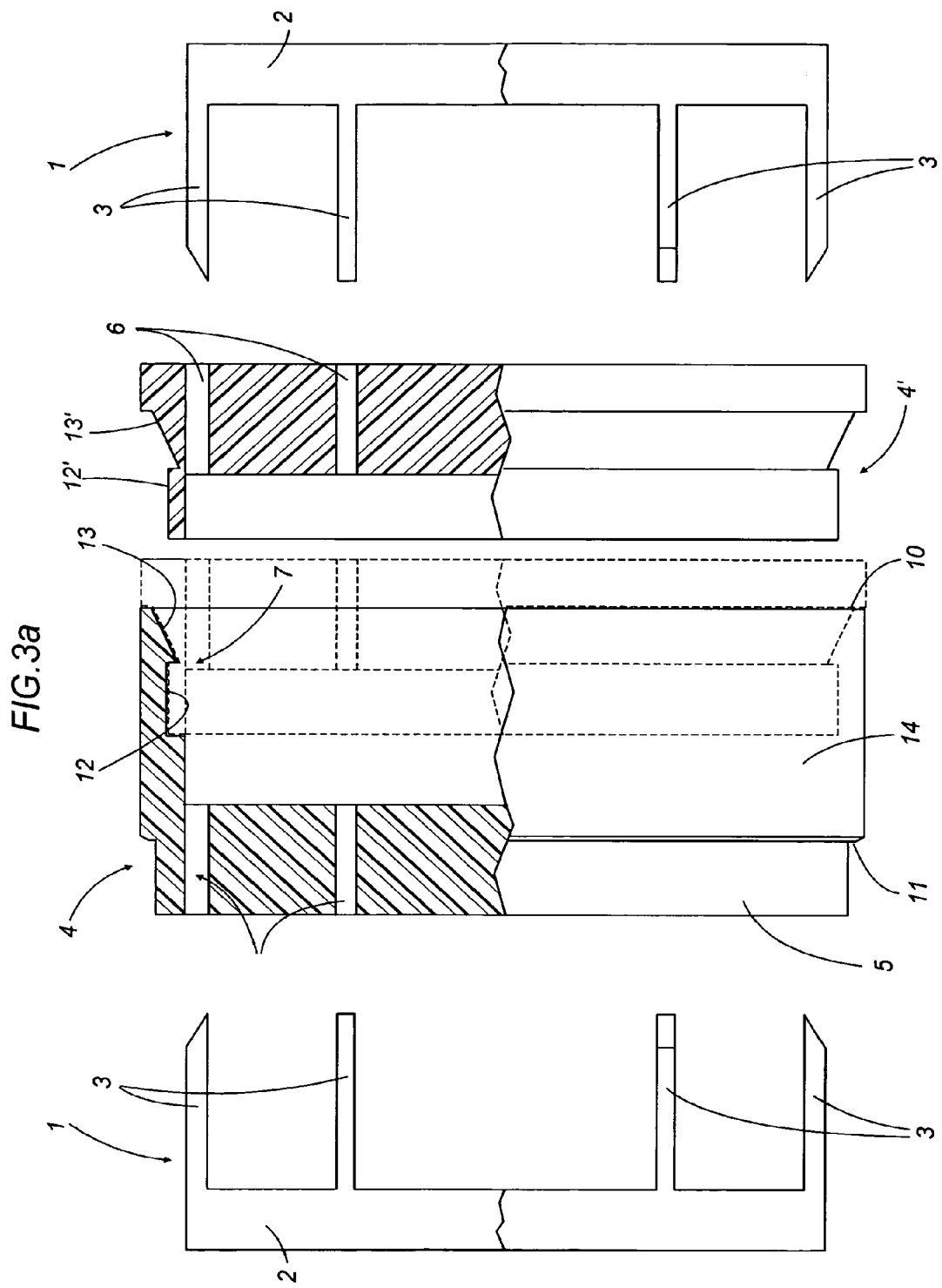
FIG. 3a shows two grafts like those of FIG. 3, with a male/female profile for reciprocal connection.

FIG. 3a, for example, shows two grafts according to the invention where the reciprocal connection does not require a third connecting cylinder but is obtained by a simple male/female connection between the recess 12 on one graft and a matching external recess 12' on the second graft.

Figure 10:
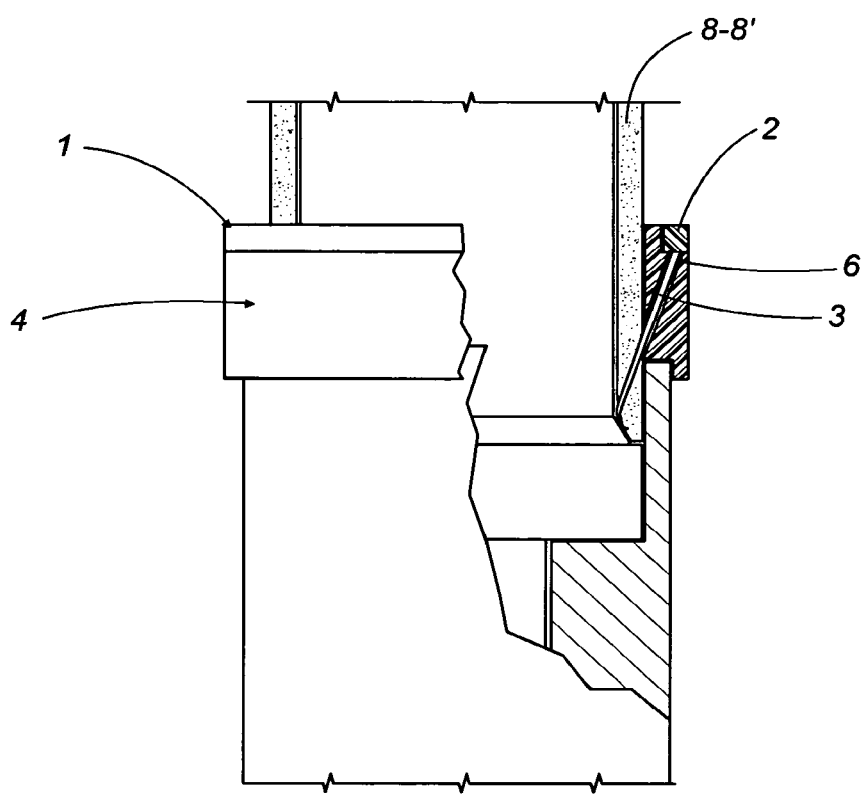
FIG. 10 shows a partial cross section of a third embodiment of a graft according to the invention.

FIG. 10 illustrates a third embodiment of a connecting cylinder 4 according to the invention where the guide holes are not parallel but inwardly converging.

In this solution, the guide holes 6' guide the legs 3 so that they pierce the portion 8/8' in a defined direction and to a defined depth as determined by appropriately choosing the length of the legs 3 and the angle of the holes 6'.

It will be understood that the connecting cylinders 4 illustrated in FIG. 9 can also have one or more of the reciprocal fastening features like the one described above.

Described below with reference to FIGS. 4 and 4a to 4d is a first embodiment of a tool 21 for applying the graft according to the invention to end portions 8/8' of a blood vessel or vascular prosthesis.

Only the working part of the applicator 21 is illustrated and it will be understood that the reciprocal movement of the different parts may be accomplished by customary means such as handles or handgrips of various kinds and combined by screw, spring, snap or other suitable means.

The applicator 21 comprises a hollow cylindrical body 22 within which there is a stem 23, that may slide on command.

The stem 23 comprises a portion of measured diameter 26 and at its top end (as illustrated in the drawing) is equipped with a nosepiece 24, which may also be of measured shape and diameter.

Preferably, the nosepiece 24 can protrude from the stem 23 by an adjustable measure, thanks, for example, to a screw coupling actuated by a slot 25 made in the nosepiece.

The stem 23 also has an external annular protrusion 27 that provides a bottom contact surface 39 for a corresponding recess 30 in the body 22, and a top surface 40 for supporting the edge 9 of the end portion 8/8' of the vessel.

In a preferred embodiment, the protrusion 27 may be connected at the top to the measured portion 26 by means of an upwardly converging collar or tapered profile 28.

The walls 41 of the recess 30 in the main body 22 have, in turn, a tapered guide profile 34, preferably inclined by 20° and replaceable or adjustable in angle, that ends at the top with an edge 29 designed to provide a reference stop against which the connecting cylinder 4 can abut.

Advantageously, when the applicator is used, the edge 9 of the vessel wall and the edge 10 of the connecting cylinder 4 are at a predetermined distance from each other and can therefore be positioned relative to each other, for example, to make the edge of one or both of the end portions protrude slightly in order to improve reciprocal contact.

Figure 4:
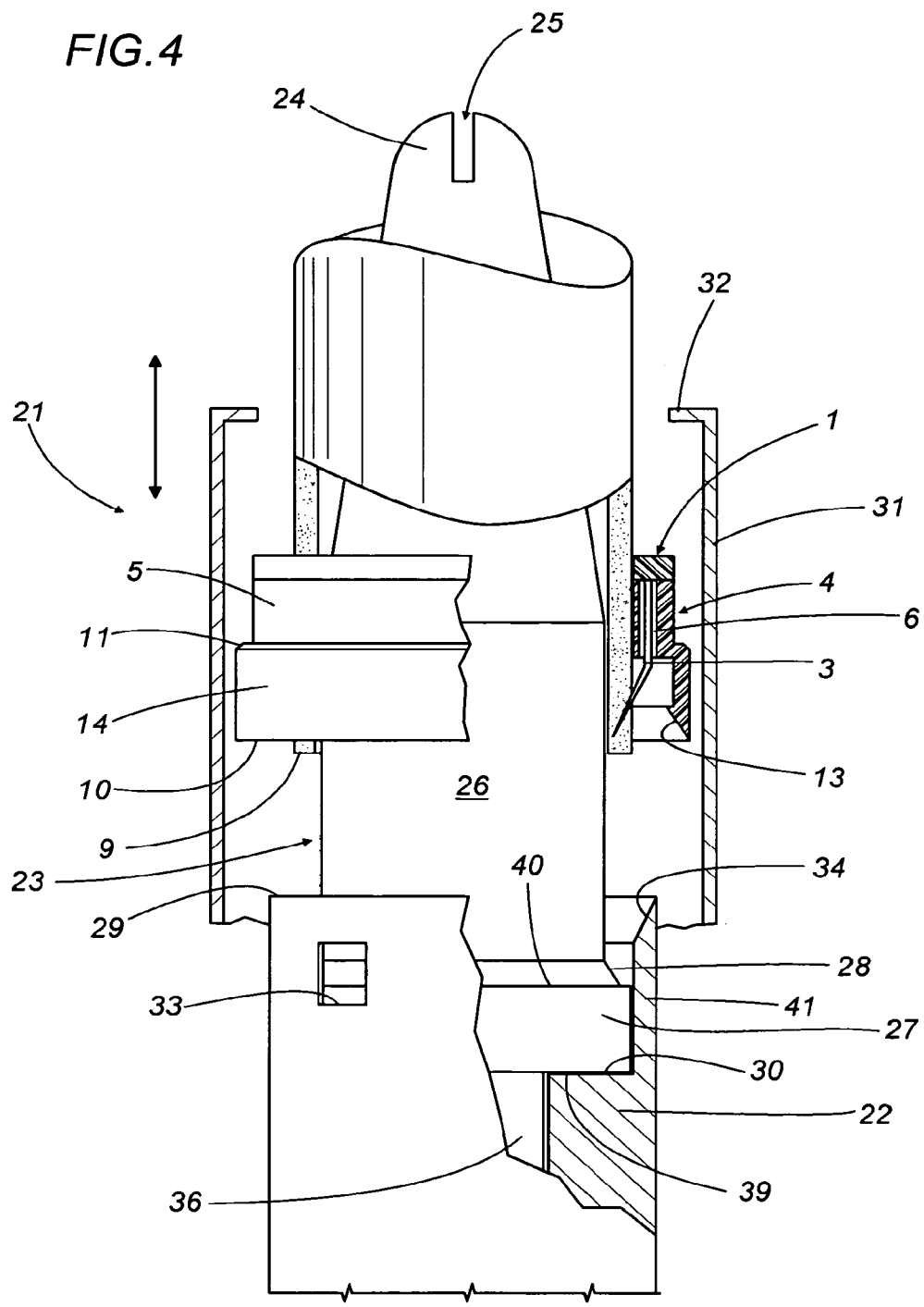
FIG. 4 illustrates a first embodiment of a device according to the invention for applying the graft of FIG. 1 or 3 to the end portions of a vessel to be connected by end-to-end anastomosis and shows the working part of the device, with some parts cut away for clarity.

FIG. 4 also schematically illustrates an element 31 that can move lengthways along the stem 23, consisting preferably of a hollow cylinder having, at the top of it, internal radial projections 32 for engaging the connecting cylinder 4.

In a preferred embodiment (illustrated schematically in FIG. 6a), the element 31 consists of two spring-opening halves 31' designed to accommodate and securely withhold a connecting cylinder 4 and to open on command in order to release the element once application has been completed.

Advantageously, in this embodiment, the graft 4 can be pre-assembled in the applicator so that the surgeon can work in depth during the anastomosis operation.

When the applicator 21 is used, one of the connecting elements 4 is inserted into the main body 22 with the front end close to the stop 29 and with the staple 1 legs 3 outside or just inside the holes 6.

The end portion 8/8' can therefore be inserted through the staple 1 and cylinder 4 and pushed against the surface 40. If necessary, this can be facilitated by moving the stem 23 so as to insert the nosepiece 24 and the measured portion 26 into the vessel end portion 8/8'.

In this configuration, the inside walls of the end portion 8/8' are in contact with the measured portion 26 of the stem 23 and the edge 9 is against the surface 40.

Advantageously, the position of the end portion 8/8' can be checked through appropriate windows 33 made in the wall of the main body 22.

At this point, the sliding element 31 can be moved so as to push the legs 3 of the staple 1 into the holes in the cylinder 4 and to move the staple 1 towards the main body 22.

As the staple 1 moves, the legs 3 meet the tapered profile 34 and are forced to bend inwardly, thus piercing the wall of the vessel end portion 8/8'.

As shown more clearly in FIG. 4c, when the mobile element 31 is near the end of its travel, the legs 3 are close to the edge 9 and just protrude on the inside of the end portion 8/8' itself, against the surface of the measured portion 26 of the stem 23.

In the last fraction of the movement, the staple legs are compressed against the tapered profile 28 and are bent back outwards.

Advantageously, this solution makes it possible to precisely gauge the end portion 8/8' that will be held by the legs 3 to the required diameter even after possible physiological collapse of the blood vessel.

Further, since the tips of the legs 3 are bent back outwards, they line up against the inside walls of the vessel, thus preventing obstruction to blood flow once the flow has been restored to the vessel.

In addition, the reliability of the graft is enhanced by the double bend of the legs 3 which opposes the tendency of the legs 3 to be expelled by the force exerted by the vessel when it contracts.

FIG. 4d illustrates the configuration of the vessel end portion 8/8' when a graft according to the invention has been applied to it.

Figure 5A:
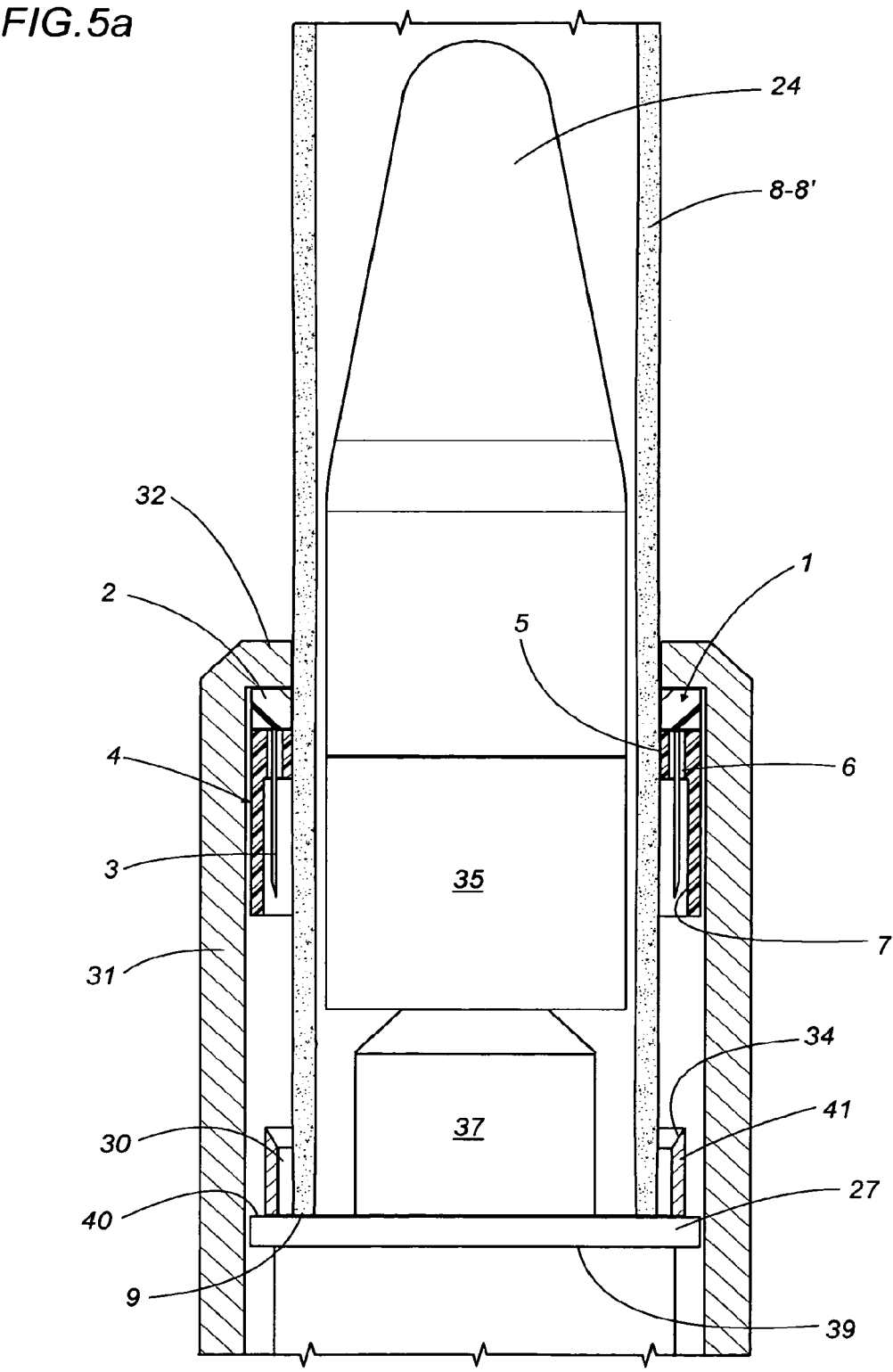
FIGS. 5a and 5b illustrate a second embodiment of an applicator according to the invention, respectively before and after application of the graft to a vessel or prosthesis.
Figure 5B:
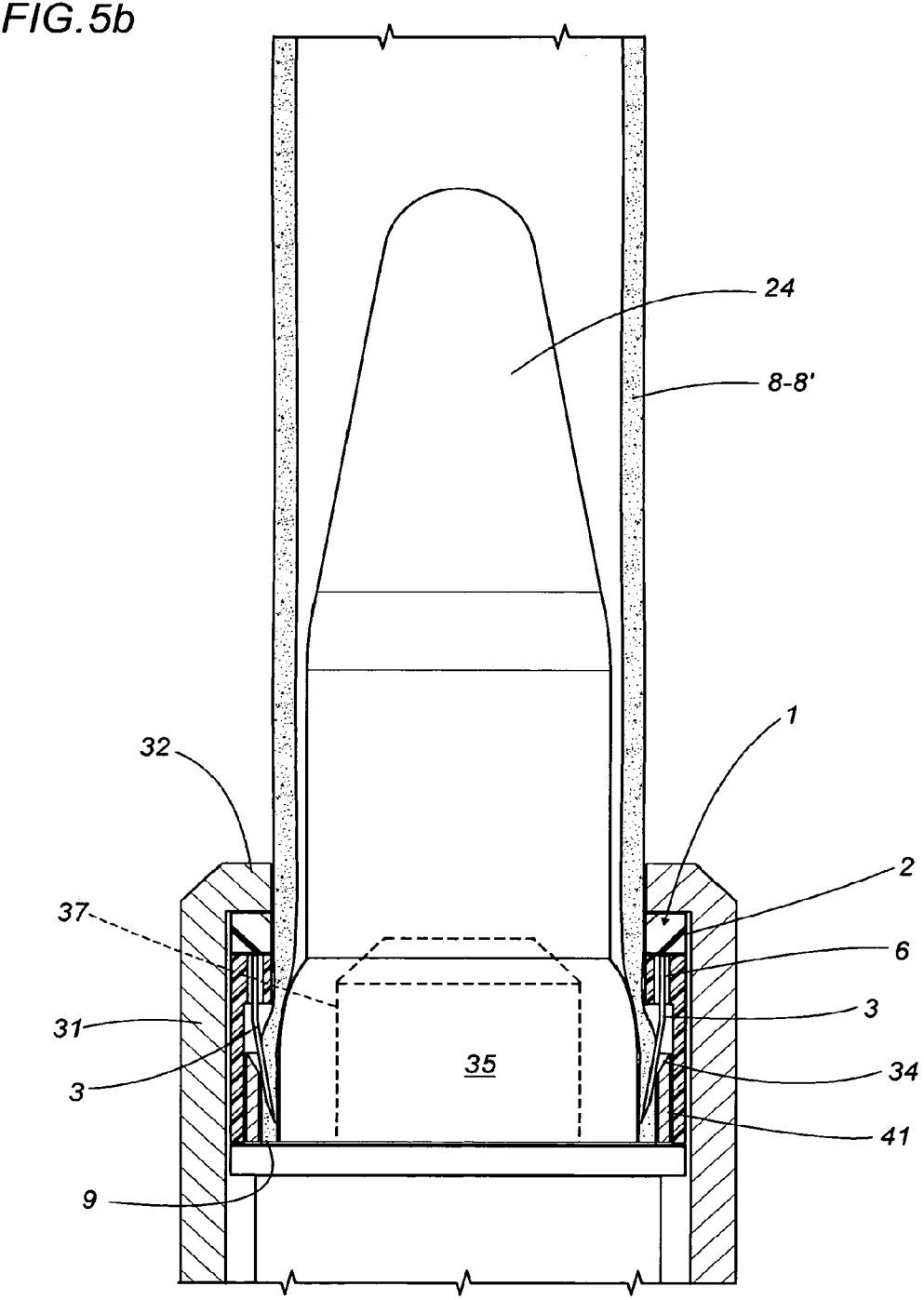

FIGS. 5a, 5b and 6 illustrate a second embodiment of an applicator, used when the vessels to be anastomosed differ in diameter.

In this embodiment, the stem 23 is equipped with a deformable element 35 between the nosepiece 24 and an abutting surface which preferably coincides with the reference surface 40 for positioning the edge 9.

As shown in more detail in FIG. 6, the nosepiece 24 may be fixed to a threaded section 36 at the end of the stem 23, whilst the stem 23 is slidable on command through a truncated cone shaped protrusion 37 that is integral with the main body 22.

During use, the nosepiece 24 (whose diameter is suitably smaller than the inside diameter of the vessel) is inserted into the end portion 8/8' and the edge 9 is brought into contact with the stop 40.

In this configuration, the stem 23 pushes the nosepiece towards the stop 40 in such a way as to force the protrusion 37 into the deformable element 35 which adopts the rounded form illustrated in FIG. 5b, pressing the wall of the end portion 8/8' against the walls 41 of the recess 30.

In the next step of stapling the vessel, the legs 3 are inserted through the holes 6, deformed by the tapered profile 34 and forced to pierce the wall of the end portion 8/8', as described above.

In this case, too, it will be understood that there may be a tapered protrusion 28 to bend the legs 3 back outwards.

It will be appreciated that this solution can advantageously be used on vessels whose inside diameters differ simply by suitably adjusting the deformation of the body 36.

FIG. 6 illustrates a possible form of handgrip 42 to drive the sliding reference element 31 lengthways.

In this example, the handgrip consists of twin pawls symmetrical about the sliding element 31 and designed to accommodate two fingers, although other shapes are imaginable.

Figure 7A:
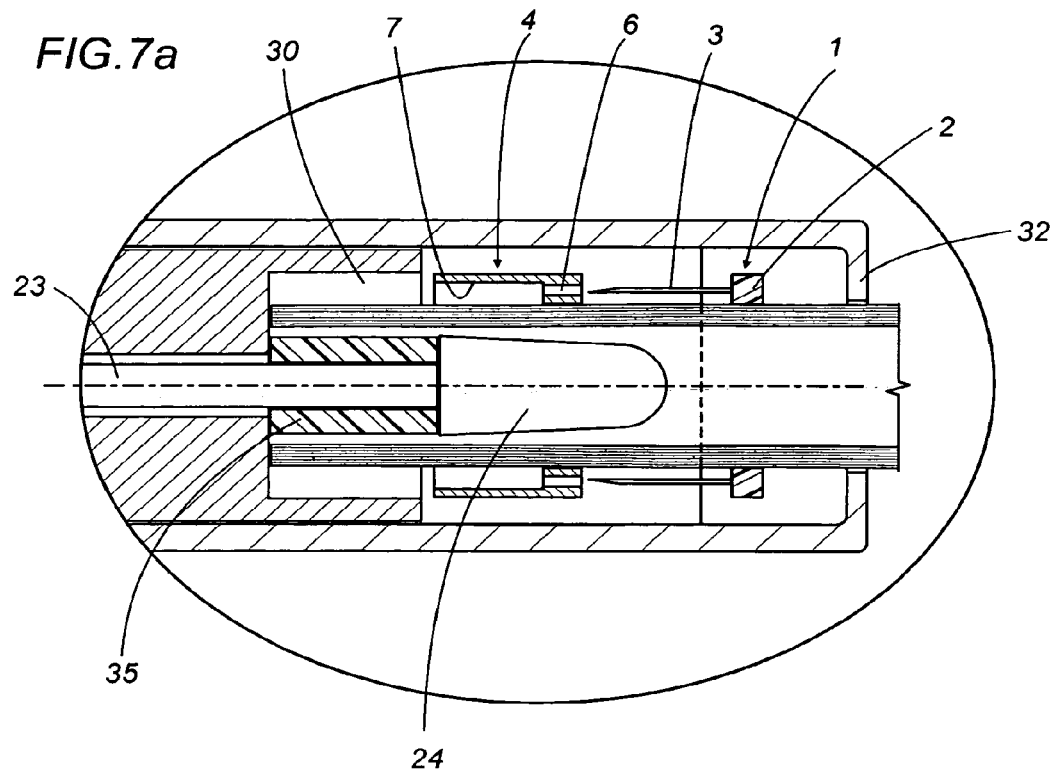
FIGS. 7a and 7b illustrate a detail of the applicator of FIG. 7, respectively before and after application of the graft to a vessel or prosthesis.
Figure 7B:
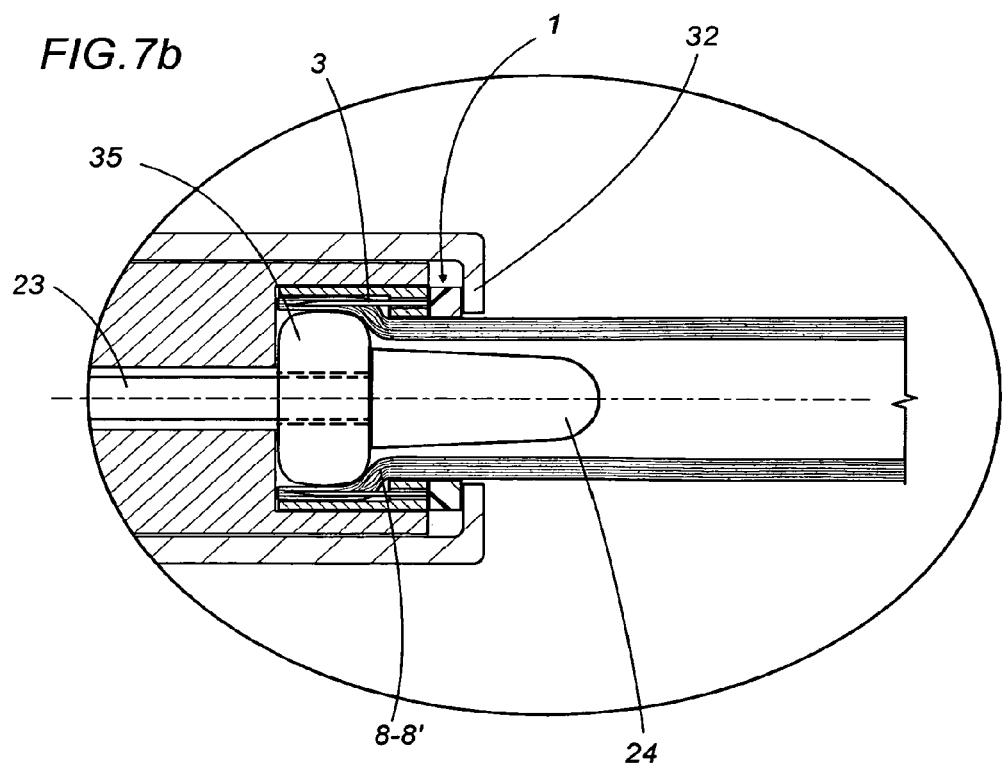

FIGS. 7a and 7b illustrate yet another embodiment of the applicator that differs from the one described above with reference to FIGS. 5a and 5b in particular in the type of mechanism used to deform the element 35.

In this embodiment, the element 35 is mounted around the stem 23 at an intermediate position between the nosepiece 24 and the bottom of the recess 30, so that it is compressed and assumes a rounded form (FIG. 7b) when the nosepiece 24 is moved closer to the recess 30.

Another difference from the embodiment illustrated in FIGS. 5a, 5b is that the recess 30 may be large enough to accommodate a connecting cylinder 4.

Thus, stapling does not necessarily occur by bending the legs 3 against the profile 34 (which, in this embodiment, may not be present). Instead, the legs 3 are inserted lengthways into the wall of the vessel end portion 8/8' when the latter is expanded by the deformable element 35 in such a way as to interfere with the movement of the legs 3.

FIG. 8 illustrates a possible configuration of an applicator according to the invention, comprising a first lever 43 integral with the main body 22, a second lever 44 pivoted to the first lever in such a way as to drive the stem 23 lengthwise to one or more positions defined by a snap lock mechanism 46.

A handgrip 45 is also provided to drive the sliding element 31 when stapling the end portion 8/8'.

FIG. 9 shows a possible embodiment of a pair of forceps for reciprocally fastening a pair of vascular grafts applied to respective portions 8/8' of an anastomosed vessel.

The forceps comprise a semicylindrical seat 48 located at one end of a central rod 49 and designed to accommodate a reciprocal coupling cylinder 16 which may be securely locked by means of an element 50 that slides on command on the rod 49 in such a way as to surmount and lock the cylinder 16 in the seat 48.

Another two semicylindrical seats 47 for housing two connecting cylinders 4 applied to respective portions 8/8' are located at the ends of two lateral rods 51 joined in compass-like fashion about the central rod 49.

During use, the end portions 8/8' of the anastomosed vessel are inserted into the seats 47, and a coupling 16 is fixed in position in the central seat 48 in such a way that, by closing the compass joint 52, the coupling 16 locks the two cylinders 4 to each other (by an interference fit or using any of the mechanisms described above) and joins the two vessel end portions, thus restoring flow to the blood vessel.

Preferably, an extractor element is also provided to facilitate disengagement of the graft, after it has been applied, by pushing the graft cylinders 4 away from the seat 48. The extractor might, if necessary, be provided by the slider 50.

As stated above, although the invention is especially advantageous for anastomosing blood vessels, the graft and the applicator described above may also be used for prosthesis applications.

This invention has been described with reference to preferred embodiments of it but it will be understood that it may be modified and adapted in several ways without thereby departing from the scope of the inventive concept.

What is claimed is:

1. An applicator for vascular grafts comprising:
a cylindrical stem (23) having a nosepiece (24), designed to precisely engage the inside surface of a blood vessel or prosthesis at least at an end portion (8,8') of the vessel or prosthesis, and an annular protrusion (27) positioned at a distance from the nosepiece (24) and defining
a first stop surface (40) extending at right angles to the cylindrical stem and designed to abut against a free front edge (9) of the end portion of the vessel or prosthesis;
a hollow cylindrical element (31) designed to accommodate at least partially the outside surface of the blood vessel or prosthesis and mobile lengthwise along the cylindrical stem and with respect to the first stop surface (40);
a body (22) coupled externally to the cylindrical stem (23) and extending within the hollow cylindrical element (31) and having an annular wall (41) protruding lengthwise from the annular protrusion (27) of the stem, to surround a stretch of the stem (23) at a radial distance therefrom, said wall (41) defining at its end
a second stop surface (29) extending at right angles to the cylindrical stem (23), spaced longitudinally and by a precise predetermined measure from the first stop surface (40), and designed to abut against a matching surface of a connecting cylinder (4) of the vascular graft, whereby the annular wall (41) is configured to surround an outer surface of the end portion (8,8') when the front edge (9) of the end portion of the vessel or prosthesis abuts against the first stop surface (40);
engagement means (32) integral with the hollow cylindrical element (31), that can be actuated in such a way as to move a piercing element (1) of a vascular graft lengthways from a first, extracted position to a second position where the graft pierces the vessel or prosthesis at least at its front edge,
wherein the hollow cylindrical element (31) is movable lengthwise with respect to the first stop surface (40) and the second stop surface (29), whereby the first stop surface (40) and the second stop surface (29) remain stationary during the movement of the hollow cylindrical element (31),
wherein a maximum diameter of the nosepiece (24) is smaller than a diameter defined by the first stop surface (40).

2. The applicator according to claim 1, comprising a tapered surface (34) of predetermined angle that is fixed with respect to the engagement means (32) in order to bend and cause to converge inwardly the piercing elements (3) as they move between the first and second position.

3. The applicator according to claim 1, wherein the stem (23) has a tapered profile (28) of predetermined angle located at the first stop surface (40) and designed to bend the piercing elements (3) back outwards.

4. The applicator according to claim 1, wherein the stem (23) has at least one portion that is variable in diameter in order to adapt to vessels whose inside diameters differ.

5. The applicator according to claim 4, wherein the variable diameter portion consists of an expansion element (35) that is deformed on command.

6. The applicator according to claim 1, wherein the longitudinal position of the nosepiece (24) is adjustable.

7. The applicator according to claim 1, wherein the wall (41) of the body (22) defines windows (33), for checking the position of the end portion (8,8') of the vessel or prosthesis.

* * * * *